United States Patent [19]

Mulder, deceased et al.

[11] 4,148,787
[45] Apr. 10, 1979

[54] ANTIDIURETICALLY EFFECTIVE POLYPEPTIDE AND A PROCESS FOR PREPARING THE SAME

[75] Inventors: Jan L. Mulder, deceased, late of Malmö, Sweden, by Anneliese Mulder, executrix; Lars A. I. Carlsson, Malmö, Sweden

[73] Assignee: Ferring AB, Malmö, Sweden

[21] Appl. No.: 849,389

[22] Filed: Nov. 8, 1977

Related U.S. Application Data

[63] Continuation-in-part of Ser. No. 799,834, May 23, 1977, abandoned.

[30] Foreign Application Priority Data

| | | | |
|---|---|---|---|
| May 24, 1976 | [SE] | Sweden | 7605853 |
| Nov. 12, 1976 | [SE] | Sweden | 7612667 |
| May 20, 1977 | [GB] | United Kingdom | 21345/77 |
| May 24, 1977 | [BE] | Belgium | 0177844 |
| May 24, 1977 | [DE] | Fed. Rep. of Germany | 2723453 |
| May 24, 1977 | [JP] | Japan | 52-59510 |

[51] Int. Cl.² .................... C07C 103/52; C07G 7/00; A61K 37/100
[52] U.S. Cl. ........................... 260/112.5 R; 424/177
[58] Field of Search ........................... 260/112.5 R

[56] References Cited

U.S. PATENT DOCUMENTS

| | | | |
|---|---|---|---|
| 3,418,307 | 12/1968 | Borssonnas et al. | 260/112.5 R |
| 3,454,549 | 7/1969 | Borssonnas et al. | 260/112.5 R |
| 3,497,491 | 2/1970 | Zaoral et al. | 260/112.5 R |

*Primary Examiner*—Delbert R. Phillips
*Assistant Examiner*—Blondel Hazel
*Attorney, Agent, or Firm*—Beveridge, DeGrandi, Kline & Lunsford

[57] ABSTRACT

Antidiuretically effective vasopressin derivates of the formula

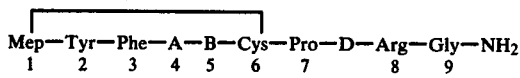

in which Mep is a 2-mercaptopropionyl residue ($-S-CH_2CH_2CO-$), and A and B are glutamine (Gln) or asparagine (Asn) and A is Gln only when B is Gln and D-arginine is in position 8.

A method for preparing the derivatives comprises the steps of gradually producing the amino acid sequence

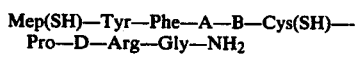

and thereafter oxidizing this amino acid sequence to the desired vasopressin derivative of the formula (I).

4 Claims, No Drawings

ANTIDIURETICALLY EFFECTIVE POLYPEPTIDE AND A PROCESS FOR PREPARING THE SAME

This application is a continuation-in-part of copending application Ser. No. 799,834, filed May 23, 1977, now abandoned the entire disclosure of which is relied on and incorporated herein by reference.

The present invention relates to antidiuretically effective polypeptides and a process for their preparation. The compounds according to the invention are antidiuretic desamino-D-arginine[8]-vasopressin derivatives of prolonged activity, free of side-effects and of the general formula I

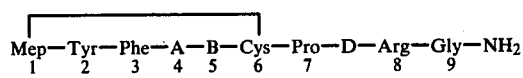

in which Mep is a 2-mercaptopropionyl residue (—S—CH$_2$CH$_2$CO—), A and B are glutamine (Gln) or asparagine (Asn) and A is Gln only when B is Gln, and D-arginine is found in position 8.

The duration of the antidiuretic activity of the vasopressin depends upon the rate of the enzymatic degradation of the intact peptide. Structure variations of the peptide which reduce the enzymatic degradation rate while the biological activity is retained are highly desirable, in particular if the resultant therapeutic effect is increased and extended. Replacement of the cysteine moiety at position 1 by Mep and replacement of L-arg at position 8 by D-arg in arginine-vasopressin has produced desamino-D-arginine[8]-vasopressin, known as DDAVP which is an analogy to vasopressin and has an extended antidiuretic effect as well as a greatly reduced effect on the smooth muscles in the vascular system and intestine as compared with vasopressin. Both of these effects are valuable in the treatment of diabetes insipidus. Apart from the above-indicated valuable effects, it is necessary, as regards women suffering from diabetes insipidus who wish to become pregnant or who are pregnant, to take into consideration the uterotonic activity. The known vasopressin derivatives have too high a uterotonic activity to be given to pregnant women without the risk of causing a miscarriage. Thus, there is a great need in the art to realize, for pregnant sufferers from diabetes insipidus, a medicine with a sufficiently low uterotonic activity in a therapeutic dose.

In view of the fact that the illness diabetes insipidus requires constant, that is to say life-long medicination, there is a risk that the patient after a period of treatment either become immune to the medicine or hypersensitive to it. In order that it be possible to continue treatment of the disease, some other corresponding medicine must in this case be used which does not result in the above-mentioned immunity or allergy on the part of the patient. However, no such alternative medicines to vasopressin and DDAVP have been previously available. The object of the present invention is, therefore, to eliminate this shortcoming. The present invention provides a new vasopressin derivative which has an antidiuretic effect of the same order of magnitude as the prior art preparations and has considerably lower uterotonic activity and, thus, a greatly improved ratio of antidiuresis/uterotonic activity. More precisely, the uterotonic activity of the preparation according to the present invention is a tenth potency lower than in prior art preparations which gives a ratio of antidiuresis/uterotonic activity which is a tenth potency higher, a fact which must be considered unique. Compounds according to the present invention may thereby be prescribed for women who suffer from diabetes insipidus and who wish to become pregnant, and may be prescribed for these women during the entire period of pregnancy, this opening entirely new horizons to this group of women.

According to the invention, the antidiuretically effective desamino-D-arginine[8]-vasopressin derivative is a derivative of the formula

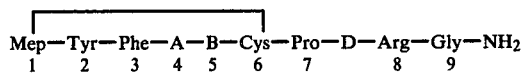

in which Mep is 2-mercaptopropionyl and A and B are glutamine (Gln) or asparagine (Asn) and A is Gln only when B is Gln.

According to a further aspect of the present invention, the vasopressin derivative is prepared in that the amino acid sequence

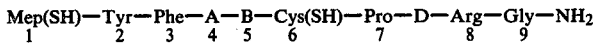

in which Mep, A and B are the same as disclosed above, is gradually produced in a per se known manner and this amino acid sequence is thereafter oxidized to form the desamino-D-arginine[8]-vasopressin derivative of formula (I).

The polypeptides according to the present invention may be used both in the form of free bases as salts of inorganic or organic acids, possibly with an addition of assistors, stabilisors and preservative additives, sweeteners, aromatic substances, wetting agents etc. for the production of application forms for perenteral, peroral, intranasal, subcutane, intramuscular and intravenous administration. Examples of usable inorganic acids are, for example, hydrochloric acid and phosphoric acid, and of usable organic acids, for example, acetic acid, citric acid and tartaric acid. Compounds with an acid function such as tannin may also be used. Suitable additives are starch, lactose, natural or cured oils, talc, glycerine etc. An advantage inherent in the new compounds is their good intranasal resorbability. This entails that the patient may in a simple and easily accessible manner dose and administer the medicine intranasally. Thus, it is not necessary to ressort to syringes for intravenous administration which is much more circumstantial and complicated.

The peptides according to the present invention are prepared using, as the starting material, a protected pentapeptide amide (II)

in which B is as above, X is a protective group for the amino group (benzyloxicarbonyl), Bzl is a protective group for the mercapto group (benzyl) of the cysteine and Y is a protective group for the guanidine nitrogen (p-toluene sulphonyl). The protective group X is removed and the pentapeptide is coupled to (III).

wherein A is as above and $ON_p$ is a p-nitrophenyl ester activity figures, data for DDAVP as a comparative compound being arbitrarily set at 1.00.

TABLE I

Relative antidiuretic activity, blood pressure activity and uterotonic activity for DDAVP analogues in relation to DDAVP

| Peptide | Activity | | | | | |
|---|---|---|---|---|---|---|
| | Antidiuresis | Protraction | Blood pressure | Uterotonic | Antidiuresis Blood pressure | Antidiuresis Uterotonic |
| DDAVP (known) | 1.00 | ++ | 1.00 | 1.00 | 1.00 | 1.00 |
| 4-Val-DDAVP (known) | 1.44 | ++ | <0.15 | 0.9 | >9.60 | 1.6 |
| 4-Asn--DDAVP | 1.26 | ++ | 0.9 | 0.09 | 1.4 | 14.0 |
| 5-Gln--DDAVP | 0.45 | ++ | 0.18 | <0.02 | 2.5 | >23 |
| 4-Asn-5--Gln-DDAVP | 0.40 | ++ | <0.30 | <0.02 | <1.3 | >20 |
| Arg-vasopressin (known) | 0.10 | — | 1450 | 1.0 | 0.00006 | 0.1 | group, for giving the protected hexapeptide (IV)

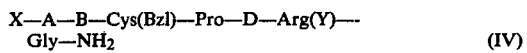
$$X-A-B-Cys(Bzl)-Pro-D-Arg(Y)-Gly-NH_2 \qquad (IV)$$

The protective group X of the peptide (IV) is removed and the hexapeptide is coupled to the tripeptide hydrazide (V)

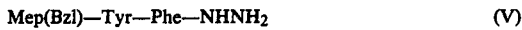
$$Mep(Bzl)-Tyr-Phe-NHNH_2 \qquad (V)$$

by the azide coupling method for obtaining the protected nonapeptide amide (VI)

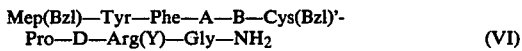
$$Mep(Bzl)-Tyr-Phe-A-B-Cys(Bzl)'-Pro-D-Arg(Y)-Gly-NH_2 \qquad (VI)$$

Treatment of the protected nonapeptide amide with an alkali metal in liquid ammonia splits off the protective groups and gives the reduced nonapeptide amide (VII)

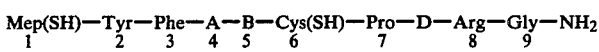
$$\underset{1}{Mep(SH)}-\underset{2}{Tyr}-\underset{3}{Phe}-\underset{4}{A}-\underset{5}{B}-\underset{6}{Cys(SH)}-\underset{7}{Pro}-\underset{8}{D-Arg}-\underset{9}{Gly}-NH_2 \qquad (VII)$$

which is oxidized in an aqueous solution with potassium ferricyanide at a pH of from 6.5–7.0 for obtaining the cyclic, biologically active peptide of the general formula (I).

Replacement of the amino acids of the vasopressin in positions 4 and 5 as above combined with a replacement of the cysteine portion at position 1 by Mep and L-arginine at position 8 by D-arginine gives the peptides (I) which, apart from good intranasal resorbability, also have increased antidiuretic activity, greatly reduced activity raising the blood pressure, good prolongation and greatly reduced uterotonic activity, as compared with vasopressin (please see Table I). Apart from arginine-vasopressin as a reference substance, DDAVP has also been included in Table I, and a known analogous 4-val-DDAVP known in the literature in the art (Chemical Abstracts: 80, 347 v (1974)). Since the curve for the log dose vis-à-vis the response for the antidiuretic peptide of the general structure (I) is not linear, it is difficult to express a conventional activity in units/mg for the D-arginine[8]-analogues as compared with vasopressin. Thus, the strenghts in Table I are expressed as relative It is apparent from Table I that the compounds according to the invention as well as 4-Asn-DDAVP display good values for antidiuresis, protraction and blood pressure as compared with the prior art compounds. Moreover, they display considerably improved values for uterotonic activity and superior values for the relationship antidiuresis/uterotonic activity. It follows that at the same time there are realized a good value for antidiuresis, minor blood pressure-increasing effect, good prolongation and extremely low uterotonic activity, which is extremely valuable for fertilized women suffering from diabetes insipidus.

The desamino-D-arginine[8]-vasopressin derivatives can be made into a therapeutic preparation in aqueous or non-aqueous solutions which contain organic or inorganic salts, acids or bases, for oral, rectal or subcutane administration.

The invention will be illustrated by means of the following embodiments for which the following points are valid unless otherwise stated.

The following abbreviations have been used:
TLC = thin layer chromatogrphy
AAA = analysis of amino acid composition
Cbz = carbobenzyloxy-group
Tos = tosyl group (p-toluensulphonyl group)

The evaporations were carried out with water suction and at 35° C. unless otherwise stated. All solvents were of reagent quality. The pH of the non-aqueous solutions was determined by moist litmus paper.

The optical angle of rotation was determined by means of a Perkin-Elmer 141 Polarimeter.

The thin layer chromatogram was run on "Merck DC-Fertigplatten Kieselgel 60" in the following system:

| A: butanol:acetic acid:water | 4:1:1 |
|---|---|
| B: butanol:pyridine:acetic acid:water | 15:10:3:6 |
| C: cyklohexane:ethylacetate:methanol | 1:1:1 |
| D: chloroform:methanol:acetic acid | 10:2:1 |
| E: chloroform:methanol:acetic acid:water | 30:20:4:6 |

Samples for the analyses of the amino acid compositions were hydrolysed in 6 M HCl in sealed, evacuated tubes at 110° C. for 24 h.

The analyses were obtained by a JEOL-5AH Automatic Amino Acid Analyser with an accuracy of ± 1.2%.

EXAMPLE 1

      (1)

Cbz—D—Arg(Tos)—Gly—OEt

A 0° C. solution of Cbz—D—Arg(Tos) (509 g, 1.10 mol), Gly—OEt.HCl (169 g, 1.21 mol) and 169 ml (1.21 mol) triethylamine in 1.81 liters of chloroform was treated with a solution of dicyclohexylcarbodiimide (227 g, 1.10 mol) in 600 ml chloroform, and was allowed to stand room temperature for 24 h. The dicyclohexylcarbamide was filtered off and washed with three portions of chloroform and the filtrate and washings were evaporated at reduced pressure. The residue was dissolved in 6 liters of ethyl acetate and washed with 1 liter portions of 0.25 n HCl (6X), H$_2$O (1X), 5% NaHCO$_3$ (3X) and H$_2$O (2X). The ethyl acetate solution was dried (Na$_2$SO$_4$) and evaporated (oil pump) and gave 554 g (92%) of the protected dipeptide ester 1.

[α]$_D^{25}$+31°(c 3.0, 95% acetic acid).

AAA: Arg, 0.85; Gly, 1.00.

TLC: Rf$^C$: 0.62, Rf$^D$: 0.67.

EXAMPLE 2

Cbz—Pro—D—Arg(Tos)—Gly—OEt      (2)

The protected dipeptide ester 1 (425 g, 0.77 mol) was dissolved in a solution of HBr (478 g) in acetic acid (2800 ml) with shaking and the solution was heated to 50° C. for 10 min. The warm solution was poured into 18 liters of diethyl ether with stirring and the white ppt was collected on a filter, washed with 2 liter portions of diethyl ether (8X), and dried in vacuo over NaOH for 5 h. The ppt was dissolved in 1260 ml of chloroform, cooled to 0° C., and triethylamine was added to pH 7.5. Crystalline Cbz—Pro—ONp (280 g, 0.758 mol) was added and the solution was kept at room temperature for one week, the pH being adjusted to 7.5 with triethylamine as needed. The solution was diluted with 5 liters of chloroform and washed with 1 liter portions of H$_2$O (1X), 1n NH$_3$(10X), H$_2$O (1X), 1n HCl (2X) and H$_2$O (3X). The chloroform solution was dried (Na$_2$SO$_4$) and evaporated (oil pump) to give the protected tripeptide ester 2 as a tan solid. The yield was 486 g (99%).

[α]$_D$ −23.0°(c 1.80, 95% acetic acid).

TLC: Rf$^C$: 0.64; Rf$^D$: 0.74.

EXAMPLE 3

Cbz—Pro—D—Arg(Tos)—Gly—NH$_2$      (3)

Redistilled ammonia was bubbled through a solution of the protected tripeptide ester 2 (210 g, 0.328 mol) in 6.9 liters of methanol for 7 h at room temperature. The ammonia and methanol were evaporated off and the oil was dissolved in 400 ml of chloroform. Ethylacetate was added (2500 ml) to ppt an oil which was triturated with 3 one liter portions of diethyl ether with scratching. The solid was collected on a filter and dried to give 168 g (83% of the protected tripeptide amide 3.

[α]$_D^{25}$ −22.6°(c 1.09, 95% acetic acid).

AAA: Pro, 1.03; Arg, 0.82; Gly, 1.00.

TLC: Rf$^C$:0.37; Rf$^D$: 0.47.

EXAMPLE 4

Cbz—Cys(Bzl)—Pro—D—Arg(Tos)—Gly—NH$_2$      (4)

A slurry of the protected tripeptide amide 3 (168 L g, 0.273 mol) in 455 ml of acetic acid was treated with a solution of HBr (240 g) in acetic acid (700 ml) for 1 h at room temperature and then poured into 9 liters of diethyl ether with stirring. The white ppt was collected on a filter and washed with 6 liters of diethyl ether. After drying in vacuo over NaOh for 6 h, the ppt was dissolved in 1070 ml dimethylformamide and the solution was cooled to 0° C. The pH of the solution was adjusted to 8.0 with triethylamine and Cbz—Cys(Bzl)—ONp (128 g, 0.27 mol) was added. After three days at room temperature the dimethylformamide was evaporated off (oil pump) and the resulting oil was dissolved in 5 liters of chloroform and washed with 1 liter portions of ln NH$_3$ (3X), ln HCl (1X) and H$_2$O (2X). The chloroform solution was dried (Na$_2$SO$_4$), concentrated to 500 ml and 1500 ml of diethyl ether was added to ppt an oil which was triturated with 2 one liter portions of diethyl ether. The solid was collected on a filter and dried to give the protected tetrapeptide amide 4. The yield was 194 g (88%).

[α]$_D^{25}$ −15.9°(c 0.91, dimethylformamide).

AAA: Cys(Bzl), 0.81; Pro, 1.02; Arg, 0.79; Gly, 1.00.

TLC: Rf$^C$: 0.48; Rf$^D$: 0.56.

EXAMPLE 5

Cbz—Asn—Cys(Bzl)—Pro—D—Arg(Tos)—Gly—NH$_2$      (5)

A slurry of the protected tetrapeptide amide 4 (190 g, 0.235 mol) in 540 ml of acetic acid was treated with a solution of HBr (380 g) in acetic acid (1450 ml) for 1.25 h and poured into 9 liters of diethyl ether with stirring. The white ppt was collected on a filter, washed with 7 liters of diethyl ether, dried for 5 h in vacuo over NaOH and dissolved in 4.5 liters of methanol. A slurry of ion-exchange resin ("IRA-410", OH$^-$; 800 ml bed) in methanol was added and the mixture was stirred for 10 min, the resin being filtered off and washed with methanol. The combined filtrate and washings were evaporated with oil which was dissolved in 800 ml of dimethylformamide. Cbz—Asn—ONp (100 g, 0.259 mol) was added, the pH was adjusted to 7.5 with triethylamine, and the solution was allowed to stand at room temperature for 4 days. The solution was concentrated to 100 ml (oil pump) and the resulting viscous oil was diluted with 150 ml warm methanol. The protected pentapeptide amide was ppt by the addition of 1 liter of ethyl acetate, collected on a filter, and washed with 2 liters of a solution of ethyl acetate and methanol (4:1) and then with 500 ml ethyl acetate. The dried peptide 5 weighed 160 g (72%).

[α]$_D^{25}$ −18.9°(c 1.10, dimethylformamide)

AAA: Asp, 0.91; Cys(Bzl), 0.72; Pro, 0.98; Arg, 0.80; Gly, 1.00.

TLC: Rf$^A$: 0.50; Rf$^C$: 0.19; Rf$^D$: 0.16.

EXAMPLE 6

Cbz—Asn—Asn—Cys(Bzl)—Pro—D—Arg(Tos)—Gly.NH$_2$      (6)

The protected pentapeptide amide 5 (923 mg, 1 mmol) was dissolved in 10 ml of 2.5n HBr in acetic acid. After 1.25 h at room temperature, the hydrobromide salt was ppt with diethyl ether, filtered off, washed on the filter with several portions of diethyl ether and dried in vacuo over NaOH. The ppt was dissolved in 8 ml dimethylformamide, cooled to 0° C., and Cbz—Asn—ONp (490 mg, 1.2 mmol) and triethylamine (0.58 ml) were added. Once the mixture had stood for 24 h at room temperature, the dimethylformamide was evaporated (oil pump), the residue was diluted with ethanol and the resultant solid was filtered off and washed with several portions of ethanol. The ppt was dried over $P_2O_5$ and gave 859 mg (83%) of the hexapeptide amide 6.

mp: 185°–187°C.
$[\alpha]_D^{25}$ −18.0°(c 1.0, dimethylformamide).
TLC: $Rf^A$: 0.43; $Rf^D$: 0.11; $Rf^E$: 0.78.

EXAMPLE 7

Cbz—Tyr(Bzl)—Phe—OMe (7)

A mixture of Cbz—Tyr(Bzl)—ONp (52.6 g, 0.10 mol), HCl·Phe—OMe (23.6 g, 0.11 mol), and triethylamine (15.3 ml, 0.11 mol) in 170 ml of dimethylformamide was allowed to stand at room temperature for 19 hours. Ethanol (600 ml) was added to the solution and the crystalline material which formed after 2.5 hours at 4° C. was collected on a filter and washed with ethanol (4×200 ml) and diethyl ether (2×200 ml). The protected dipeptide ester 7 weighed 51.8 g (91%) after drying.

mp 179°–181° C.
$[\alpha]_D^{25}$ −18.7°(c 1.05, dimethylformamide).
TLC: $Rf^C$: 0.84; $Rf^D$: 0.90.

EXAMPLE 8

HCl·Tyr—Phe—OMe (8)

A suspension of Cbz—Tyr(Bzl)—Phe—OMe (20.4g, 0.036 mol) and 1 g Pd in 400 ml methanol containing 7.2 ml 5n HCl (0.036 mol), was hydrogenated at atmospheric pressure for 24 hours at room temperature, an additional 1 g of pd was added and hydrogenation continued for 10 hours. The palladium was filtered off and washed with methanol on the filter. The combined methanol filtrate and washings were evaporated, the oil which was obtained was diluted with diethyl ether and allowed to stand at 4° C. overnight. The crystalline hydrochloride salt 8 was collected on a filter, washed with diethyl ether and dried to give 13.1 g (97%).

mp:—.
$[\alpha]_D^{25}$ +2.8°(c 1.0, dimethylformamide).
TLC: $Rf^C$: 0.54, $Rf^D$: 0.32.

EXAMPLE 9

Mep(Bzl—Tyr—Phe—OMe (9)

A 0° C. solution of HCl·Tyr—Phe—OMe (5.0 g, 13.2 mmol), Mep(Bzl)—ONp (4.6 g, 13.2 mmol) and triethylamine (1.85 ml, 13.2 mmol) in 40 ml of dimethylformamide was allowed to stand at room temperature for 2 days. The dimethylformamide was removed in vacuo and the residue was dissolved in 100 ml of chloroform. The chloroform solution was washed with 25 ml portions of 1 n $NH_3$ (5X), 1 n HCl (1X) and $H_2O$ (2X), dried ($Na_2SO_4$) and evaporated to give 6.2 g (90% of 9).

mp 135°–136° C.
TLC: $Rf^A$: 0.92; $Rf^C$: 0.81; $Rf^D$: 0.80.

EXAMPLE 10

Mep(Bzl)—Tyr—Phe—NHNH$_2$ (10)

A solution of Mep(Bzl—Tyr—Phe—OMe (3.0 g, 5.8 mmol) and $NH_2NH_2 \cdot H_2O$ (1.5 ml, 30 mmol) in a mixture of 50 ml methanol and 20 ml of dimethylformamide was allowed to stand at room temperature for 24 hours. The crystalline hydrazide 10 was collected on a filter, washed with 6 portions of methanol and dried in vacuo over $H_2SO_4$ to give 2.1 g (70%) of 10.

EXAMPLE 11

Mep(Bzl)—Phe—Asn—Asn—Cys(Bzl)—
Pro—D—Arg(Tos)—Gly—NH$_2$ (11)

The protected hexapeptide amide 6 (518 mg, 0.5 mmol) was dissolved in 10 ml 2.5 M HBr in acetic acid. After 1.5 hours the hydrobromide salt was ppt with diethyl ether, collected on a filter, washed on the filer with several portions of diethyl ether and dried in vacuo over NaOH. The salt was dissolved in 5ml dimethylformamide, the solution was basified to pH 8.0 with triethylamine and cooled to −15° C. This solution was added to a −15° C. solution of the azide prepared in situ from the hydrazide 10 (0.55 mmol, 286 mg) with isoamylnitrite. The reaction mixture was stirred at −15° C. for 2 hours, the pH was adjusted to 8.0 with triethylamine and the reaction mixture was kept at 4° C. for 24 hours. The solution was concentrated to 1 ml in vacuo, diluted with 15 ml ethanol and the product was allowed to separate at 4° C. overnight. The ppt was collected on a filter, washed with several portions of ethanol and dried and gave 550 mg (79%) of the protected nonapeptide amide 11.

mp 203°–205° C.
$[\alpha]_D^{25}$ −26.9° (c 0.5., acetic acid).
TLC: $Rf^A$: 0.53; $Rf^B$; $Rf^B$: 0.74.

EXAMPLE 12

(Asn$^4$)—desamino—D—Arg$^8$vasopressin
(4—Asn—DDAVP) (12)

A solution of the protected nonapeptide amide 11 (250 mg, 0.18 mmol) in 200 ml NH$_3$ at −40° C., was treated intermittently with sodium (drawn up into a small bore pipette) until a blue colour remained in the solution on removal of the sodium. The permanent blue colour was discharged after 2 min by the addition of 190 mg ammonia chloride. The ammonia was evaporated off in a weak nitrogen gas stream. The residue was extracted with two 20 ml portions of ethyl acetate, dissolved in 300 ml $H_2O$, and the pH of the solution was adjusted to 6.8 with acetic acid. Oxidation was performed at pH 6.8 by the addition of 3.6 ml 0.1 M $K_3Fe(CN)_6$. After stirring for 10 min a 50 ml bed of IRA-400 (Ac−) ion-exchange resin was added to the yellow solution, the suspension was stirred for 30 min and the resin was filtered off. The ion-exchange resin was washed with several portions of water and the combined filtrate and washings were acidified to pH 3.9 and lyophilized.

200 mg of the lyophilizate was dissolved in 10 ml 50% acetic acid, applied to a 2.5×114.5 cm column of Sephadex G-15 which had been equilibrated with 50% acetic acid. The flow rate was 100 ml/h. The peak, centered at 240 ml, was collected, diluted with water and lyophilized to give 87 mg of desalted peptide 12.

86 mg of the desalted peptide 12 was dissolved in 10 ml 0.2 M acetic acid and applied to a 2.5×112 cm column of Sephadex G-15, which hade been equilibrated with 0.2 M acetic acid. The flow rate was 100 ml/h. The fractions corresponding to the single peak (centered at 510 ml, 3.90 $V_o$) were collected and lyophilized to give 43.5 mg of 12.

$[\alpha]_D^{25}$ −53.7° (c 0.2068, 1% acetic acid).

AAA: Tyr 1.05; Phe 1.10; Asp 2.12; Pro 0.99; Arg 1.04; Gly 1.00.

TLC: $Rf^A$: 0.21; $Rf^B$: 0.51; $Rf^E$: 0.36.

All symbols follow the IUPAC-IUB Commission on Biochemical Nomenclature Symbols for Amino-Acid Derivatives and Peptides Recommendations (J. Biol. Chem, 247, 977 (1972)).

EXAMPLE 13

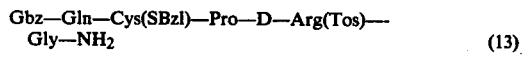
Gbz—Gln—Cys(SBzl)—Pro—D—Arg(Tos)—Gly—NH₂ (13)

A slurry of the protected tetrapeptide (4 (4.0 g, 4.95 mmol) in 15 ml of acetic acid was treated with a solution of HBr (12 g) in acetic acid (55 ml) for 1 hour and was then poured into 300 ml of diethyl ether with stirring. The white ppt was collected on a filter, washed with 200 ml diethyl ether, dried for 5 h in vacuo over NaOH and dissolved in 125 ml methanol. A slurry of ion-exchange resin ("IRA-420", OH−, 40 ml bed) in methanol was added and the mixture was stirred for 10 min, the resin being then filtered off and washed with methanol. The combined filtrates and washings were evaporated to an oil which was dissolved in 20 ml dimethylformamide. Cbz—Gln—ONp (2.0g, 4.95 mmol) was added, the pH was adjusted to 7.5 with triethylamine and the solution was then allowed to stand at room temperature for 1 day. The solution was concentrated to 5 ml (oil pump) and the resulting viscous oil was diluted with 5 ml methanol. The protected pentapeptide amide was ppt by addition of 50 ml ethyl acetate, collected on a filter, and washed with 50 ml of a solution of ethyl acetate and methanol (4:1) and then with 100 ml ethyl acetate. The dried peptide 13 weighed 2.94 g (63%)

$[\alpha]_D^{25}$ 20.2° (c 0.960 dimethylformamide).

TLC: $Rf^A$: 0.60; $Rf^C$: 0.28; $Rf^D$: 0.27.

EXAMPLE 14

Cbz—Gln—Gln—Cys(Bzl)—Pro—D—Arg—(Tos)—Gly—NH₂ (14)

The protected pentapeptide amide 13 (1.05 g, 1.12 mmol) was dissolved in 14 ml 2.5 n HBr in acetic acid. After 1 hour at room temperature, the hydrobromide salt was ppt with diethyl ether, filtered off, washed on the filter with several portions of diethyl ether and dried in vacuo over NaOH. The ppt was dissolved in 12 ml of dimethylformamide, cooled to 0° C. and Cbz—Gln—ONp (0.51 g, 1.25 mmol) and triethylamine (1 ml) were added. Once the mixture had stored for 24 hours at room temperature, the dimethylformamide was evaporated (oil pump), the residue was diluted with ethanol and the obtained solid was filtered and washed on the filter with several portions of ethanol. The ppt was dried over P₂O₅ and gave 1.04 g (87%) of the hexapeptide amide 14.

mp 155°-160° C.

$[\alpha]^{25}$ 26.8° (c 0.537 dimethylformamide).

TLC: $Rf^A$: 0.45; $Rf^D$: 0.10.

EXAMPLE 15

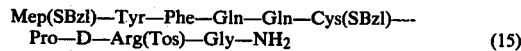
Mep(SBzl)—Tyr—Phe—Gln—Gln—Cys(SBzl)—Pro—D—Arg(Tos)—Gly—NH₂ (15)

The protected hexapeptide amide 14 (400 mg, 0.38 mmol) was dissolved in 15 ml 2.3 n HBr in acetic acid. After 1 hour the hydrobromide salt was ppt with diethyl ether, collected on a filter, washed on the filter with several portions of diethyl ether, and dried in vacuo over NaOH. The salt was dissolved in 5 ml dimetylformamide, the solution was basified with triethylamine (0.5 ml) and cooled to −10° C. This solution was added to a −15° C. solution of the azide prepared starting from the hydrazide 10 (260 mg, 0.50 mmol) in situ with isoamylnitrite. The reaction mixture was stirred at −15° C. for 2 hours, the pH was adjusted to 8.0 with triethylamine and the reaction solution was kept at 4° C. for 24 hours. The dimethylformamide was removed (oil pump) and the residue was treated with ethanol. Once the mixture had been allowed to stand overnight at 4° C., the ppt was collected on a filter, washed with several portions of ethanol and diethyl ether and dried to give 285 mg (53%) of the protected nonapeptide 15.

mp 190°-195° C.

$[\alpha]_D^{25}$ −32.8° (c 0.470, 95% acetic acid).

TLC: $Rf^A$: 0.51; $Rf^B$ 0.80; $Rf^E$: 0.93.

EXAMPLE 16

(Gln⁵)—desamino—D—Arg⁸—vasopressin (5-Gln-DDAVP) (16)

A solution of the protected nonapeptide amide 15 (175 mg, 0.123 mmol) in 100 ml NH₃ at −40° C. was treated intermittently with sodium (drawn up into a small bore pipette) until a blue colour remained in the solution after removal of the sodium. The permanent blue colour was discharged after 2 min by the addition of 150 mg of ammonium chloride. The ammonium was removed in a weak nitrogen gas stream. The residue was extracted with two portions of ethyl acetate (at 20 ml), dissolved in 250 ml of water and the pH of the solution was adjusted to 6.8 with acetic acid. The oxidation was carried out at pH 6.8 by addition of 2.5 ml 0.1 M K₃Fe(CN)₆. After stirring for 10 min., a 50 ml bed of IRA-400 (Ac)− ion exchange resin was added to the yellow solution, the suspension was stirred for 10 min and the resin was filtered off. The resin was washed with several portions of water and the combined filtrates and washings were acidified to pH 3.9 and lyophilized. 150 mg of the lyophilizate was dissolved in 10 ml 50% acetic acid, applied to a 2.5×114.5 cm Sephadex G-15 column which had been equilibrated with 50% acetic acid and eluted with the same solvent at a flow rate of 100 ml/h. The major peak detected at 280 nm, centered at 220 ml, was collected, diluted with one volume of water and lyophilized to give 90 mg. The desalted peptide was dissolved in 10 ml 0.2 M acetic acid, applied to a 2.5 × 105.0 cm Sephadex G-15 column, which had been equilibrated with 0.2 M acetic acid, and eluted with the same solvent at a flow rate 100 ml/h. The fractions corresponding to the peak at 2.63$V_o$, were collected and lyophilized to give 62 mg of 16.

$[\alpha]_D^{25}$ −59.9° (c 0.291, 1% acetic acid).

AAA: Tyr 1.03; Phe 1.06; Gln 2.01; Pro 1.06; Arg 0.96; Gly 1.00.

TLC: $Rf^A$: 0.14; $Rf^B$: 0.48; $Rf^E$: 0.51.

EXAMPLE 17

Cbz—Asn—Gln—Cys(SBzl)—Pro—D—Arg(Tos-)—Gly—NH₂ (17)

The protected pentapeptide amide 13 (1.05 g, 1.12 mmol) was dissolved in 14 ml 2.5 n HBr in acetic acid. After 1 h at room temperature, the hydrobromide salt was ppt with diethyl ether, filtered off, washed on the filter with several portions of diethyl ether and dried in vacuo over NaOH. The ppt was dissolved in 12 ml dimethylformamide, cooled to 0° C. and Cbz—Asn—ONp (0.51 g, 1.25 mmol) and triethylamine (1 ml) were added. Once the mixture had stood for 24 h at room temperature, the dimethylformamide was evaporated (oil pump), the residue was diluted with ethanol and the thus obtained solid was filtered off and washed on the filter with several portions of ethanol. The ppt was dried over P₂O₅ and gave 0.87 g (74%) of the hexapeptide amide 17.

mp: 175°–180° C.
$[\alpha]_D^{25}$ −24.9° (c 0.694 dimethyformamide).
TLC: Rf⁴: 0.45; Rf$^D$: 0.10.

EXAMPLE 18

Mep(SBzl)—Tyr—Phe—Asn—Gln—Cys(SBzl)—Pro—D—Arg(Tos)—Gly—NH₂ (18)

The protected hexapeptide amide 17 (400 mg, 0.38 mmol) was dissolved in 15 ml 2.3 n HBr in acetic acid. After 1 h the hydrobromide salt was ppt in diethyl ether, collected on a filter, washed on the filter with several portions of diethyl ether and dried in vacuo over NaOH. The salt was dissolved in 5 ml dimethylformamide, the solution was basified with triethylamine (0.5 ml) and cooled to −10° C. This solution was added to −15° C. solution of the azide prepared starting from the hydrozide 10 (260 mg, 0.50 mmol) in situ with isoamylnitrite. The reaction solution was stirred at −15° C. for 2 h, the pH was adjusted to 8 with triethylamine and the reaction mixture was kept at 4° C. for 24 h. The dimethyformamide was removed (oil pump) and the residue was treated with ethanol. Once the mixture had been allowed to stand overnight at 4° C., the ppt was collected on a filter, washed with several portions of ethanol and diethylether and dried to give 185 mg (35%) of the protected nonapeptide 18.

mp: 210°–215° C.
$[\alpha]_D^{25}$ −28.3° (c 0.530 dimethylformamide).
TLC: Rf⁴; 0.51; Rf$^B$: 0.80; Rf$^E$: 0.91.

EXAMPLE 19

(Asn⁴—Gln⁵)—desamino—D—Arg⁸—vasopressin(-4—Asn—5—Gln—DDAVP) (19)

A solution of the protected nonapeptide amide 18 (100 mg, 0.071 mmol) in 100 ml NH₃ at −40° C. was treated intermittently with sodium (drawn up into a small bore pipette) until a blue colour remained in the solution on removal of the sodium. The permanent blue colour was discharged after 2 min by the addition of 140 mg ammonium chloride. The ammonium was removed by means of a weak nitrogen gas stream. The residue was extracted with 20 ml portions of ethyl acetate, dissolved in 200 ml of water and the solution was adjusted to pH 6.8 with acetic acid. The oxidation was carried out at pH 6.8 by the addition of 1.5 ml of 0.1 M K₃Fe(CN)₆. After stirring for 10 min, a 50 ml bed of IRA-400 (Ac⁻) ion-exchange-resin was added to the yellow solotion, the suspension was stirred for 10 min and the resin was filtered off. The ion-exchange-resin was washed with several portions of water and the combined filtrates and washings were acidified to pH 3.9 and lyophilized. 70 mg of the lyophilizate was dissolved in 10 ml of 50% acetic acid, applied to a 2.5×114.5 cm Sephadex G-15 column which had been equilibrated with 50% acetic acid and eluted with the same solvent at a flow rate of 100 ml/h. The major peak, detected at 280 nm, centered at 245 ml, was collected, diluted with one volume of water and lyophilized to give 54 mg. The desalted peptide (54 mg) was dissolved in 10 ml 0.2 M acetic acid, applied to a 2.5×105.0 cm Sephadex G-15 column which hade been equilibrated with 0.2 M acetic acid, and eluted with the same solvent at a flow rate of 100 ml/h. The fractions corresponding to the peak at 2.84 V$_o$ were collected and lyophilized to give 30 mg of 19.

$[\alpha]_D^{25}$ −54.3° (c 0.287, 1% acetic acid).
AAA: Tyr 1.07; Phe 1.11; Gln 1.03; Pro 1.03; Arg 0.99; Gly 1.00; Asp 0.98.
TLC: Rf⁴: 0.18; Rf$^B$: 0.48; Rf$^E$: 0.53.

What we claim and desire to secure by Letters Patent is:

1. A desamino-D-arginine⁸-vasopressin derivative, wherein the derivative has the formula

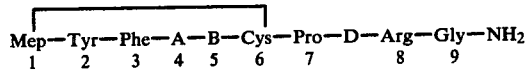

in which Mep is 2-mercaptopropionyl and A and B are glutamine (Gln) or asparagine (Asn) and A is Gln only when B is Gln.

2. Vasopressin derivative as recited in claim 1, wherein A is Asn and B is Asn.

3. Vasopressin derivative as recited in claim 1, wherein A is Asn and B is Gln.

4. Vasopressin derivative as recited in claim 1, wherein A is Gln and B is Gln.